United States Patent
Adolfsen et al.

(10) Patent No.: US 10,208,340 B2
(45) Date of Patent: *Feb. 19, 2019

(54) RANDOM ACCESS SYSTEM AND METHOD FOR POLYMERASE CHAIN REACTION TESTING

(71) Applicant: Siemens Healthcare Diagnostics Inc., Tarrytown, NY (US)

(72) Inventors: Robert Adolfsen, Pine, AZ (US); Nicolae Dumitrescu, Stamford, CT (US); Michael Avdenko, Rochester, NY (US); Dario Svenjak, Yorktown Heights, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/848,108

(22) Filed: Dec. 20, 2017

(65) Prior Publication Data

US 2018/0112254 A1 Apr. 26, 2018

Related U.S. Application Data

(60) Continuation of application No. 15/490,935, filed on Apr. 19, 2017, now Pat. No. 9,868,984, which is a division of application No. 14/529,271, filed on Oct. 31, 2014, now Pat. No. 9,656,265, which is a division of application No. 12/447,932, filed as application No. PCT/US2007/023057 on Nov. 1, 2007, now Pat. No. 8,895,267.

(60) Provisional application No. 60/856,453, filed on Nov. 3, 2006.

(51) Int. Cl.
| | |
|---|---|
| *C12M 1/00* | (2006.01) |
| *C12Q 1/686* | (2018.01) |
| *B01L 7/00* | (2006.01) |
| *C12Q 1/6806* | (2018.01) |
| *B01L 3/00* | (2006.01) |

(52) U.S. Cl.
CPC .......... *C12Q 1/686* (2013.01); *B01L 7/52* (2013.01); *B01L 7/54* (2013.01); *C12Q 1/6806* (2013.01); *B01L 3/5082* (2013.01); *B01L 2200/025* (2013.01); *B01L 2200/147* (2013.01); *B01L 2300/0609* (2013.01); *B01L 2300/0654* (2013.01); *B01L 2300/10* (2013.01); *B01L 2300/168* (2013.01); *B01L 2300/1827* (2013.01); *B01L 2300/1838* (2013.01); *B01L 2300/1894* (2013.01)

(58) Field of Classification Search
CPC ......... B01L 2200/025; B01L 2200/147; B01L 2300/0609; B01L 2300/0654; B01L 2300/10; B01L 2300/168; B01L 2300/1827; B01L 2300/1838; B01L 2300/1894; B01L 3/5082; B01L 7/52; B01L 7/54; C12Q 1/6806; C12Q 1/686; H05K 999/99
USPC ...................................................... 435/283.1
See application file for complete search history.

(56) References Cited

U.S. PATENT DOCUMENTS

| | | | |
|---|---|---|---|
| 6,337,435 B1 | 1/2002 | Chu et al. | |
| 6,509,186 B1 | 1/2003 | Zou et al. | |
| 6,562,568 B1 | 5/2003 | Kleiber et al. | |
| 6,599,484 B1 | 7/2003 | Zigler et al. | |
| 6,855,499 B1 | 2/2005 | Nargessi | |
| 2003/0104438 A1* | 6/2003 | Eyre | C12Q 1/6851 435/6.18 |
| 2004/0086930 A1 | 5/2004 | Tereba et al. | |
| 2004/0161788 A1 | 8/2004 | Chen et al. | |
| 2004/0166513 A1* | 8/2004 | Slepnev | C12Q 1/6851 435/6.14 |
| 2005/0186585 A1 | 8/2005 | Juncosa et al. | |
| 2006/0186055 A1 | 8/2006 | Kusumoto et al. | |
| 2008/0138251 A1 | 12/2008 | Dumitrescu | |
| 2009/0042281 A1 | 2/2009 | Chang et al. | |

(Continued)

FOREIGN PATENT DOCUMENTS

| | | |
|---|---|---|
| GB | 2360088 | 12/2001 |
| JP | 2001509256 | 7/2001 |
| JP | 2004317363 | 11/2004 |

(Continued)

OTHER PUBLICATIONS

Liao C-S et al: "Micromachined polymerase chain reaction system for multiple DNA amplification of upper respiratory tract infectious diseases" Biosensors and Bioelectronics, 20: 7, pp. 1341-1348, (2005).

(Continued)

*Primary Examiner* — Cynthia B Wilder

(57) ABSTRACT

A random access, high-throughput system and method for preparing a biological sample for polymerase chain reaction (PCR) testing are disclosed. The system includes a nucleic acid isolation/purification apparatus and a PCR apparatus. The nucleic acid isolation/purification apparatus magnetically captures nucleic acid (NA) solids from the biological sample and then suspends the NA in elution buffer solution. The PCR testing apparatus provides multiple cycles of the denaturing, annealing, and elongating thermal cycles. More particularly, the PCR testing apparatus includes a multi-vessel thermal cycler array that has a plurality of single-vessel thermal cyclers that is each individually-thermally-controllable so that adjacent single-vessel thermal cyclers can be heated or cooled to different temperatures corresponding to the different thermal cycles of the respective PCR testing process.

8 Claims, 5 Drawing Sheets

(56) References Cited

U.S. PATENT DOCUMENTS

2009/0130745 A1   5/2009   Williams et al.

FOREIGN PATENT DOCUMENTS

| JP | 2005523692 | 8/2005 |
| WO | 2005008209 | 1/2005 |

OTHER PUBLICATIONS

International Search Report WO2008/057375 dated Sep. 3, 2008.

* cited by examiner

RANDOM ACCESS SYSTEM AND METHOD FOR POLYMERASE CHAIN REACTION TESTING

STATEMENT REGARDING FEDERALLY SPONSORED RESEARCH OR DEVELOPMENT (Not Applicable)

BACKGROUND OF THE INVENTION

The present invention relates to a system and method for isolating and purifying a biological sample and for testing the biological sample, and, more particularly, to a high-throughput, random access system and method for isolating and purifying nucleic acid contained in a biological sample and for testing the biological sample, such as by polymerase chain reaction testing.

Polymerase chain reaction (PCR) testing is a universally-accepted and widely-practiced laboratory method for replicating or amplifying the concentration of nucleic acid (NA), such as DNA, in a test tube. Replication/amplification takes place in an aqueous solution containing a concentration of DNA molecules. Pre-determined amounts of the polymerase enzyme, oligonucleotide primers, tri-phosphates of the four nucleic acids or substrates, activators, and stabilizers are then added to the aqueous solution, which is then subject to three thermal cycles, referred to as the denaturing cycle, the annealing cycle, and the elongation cycle.

During the first, denaturing cycle, the DNA double helix in aqueous solution is melted between about 90 and 95 degrees Centigrade (° C.) so that each strand of the double helix is separated from the other. During the second, annealing cycle, the denatured aqueous solution is cooled to a temperature between about 50 and about 65° C., causing the oligonucleotide primers to attach to complementary nucleotide sequences of each denatured DNA strand. Finally, during the elongation cycle, DNA double helixes are re-formed by elongation of the primers at a temperature between about 70 and about 72° C. More specifically, a thermostable polymerase, such as Taq-polymerase, bonds nucleotides to the primer templates attached to the complementary nucleotide sequences, which forms two new DNA double helixes where before there was just one. Accordingly, with every complete cycle, there is a doubling of the number of DNA molecules, so, the number of DNA molecules after n cycles is equal to $2^n$.

The duration of each of the three thermal cycles is very brief and typically measured in seconds. For example, the DNA molecules melt instantaneously at about 95° C. during the denaturing cycle. If the primers are available in sufficient concentration, primer hybridization during the annealing cycle only requires about one (1) or two (2) seconds. Finally, re-formation during the elongation cycle can occur at a bonding rate of about 80 per second. Hence, the elongation cycle needs only about two (2) seconds. Thus, theoretically, each PCR cycle requires about five (5) seconds to complete.

In practice, however, the duration of each thermal cycle depends on the rate of heat transfer, to heat or cool the aqueous solution at the pre-determined thermal cycle temperature. Variables that can affect the heating/cooling rates include, inter alia, the volume of the solution, the concentration of the aqueous solution, the thermal conductivity of the vessel holding the NA in aqueous solution, the thermal conductivity of the apparatus holding the vessel, and the method of applying and removing heat, e.g., by conduction or convection.

Conventionally, PCR testing is performed in "batches". For example, typically, a thermal cycling device, such as a PCR plate, holds 96 vessels in a closely-spaced, 8×12 vessel-well pattern. Batch processing and large thermal cycling devices used for batch processing, however, have several shortcomings.

First, testing is not begun until each well in the thermal cycling device is filled with a vessel, which adds time. Second, because the pre-determined temperatures for the annealing and elongation thermal cycles vary depending on the nucleic acid being tested for, such as HIV, HCV, HDB, and so forth, testing is not begun until each well in the thermal cycling device is filled with a vessel containing an aqueous solution having a concentration of the same DNA molecule, which adds even more time. Third, because the vessels and thermal cycling device are introduced at once as a unit, the amount of time to bring the vessels and thermal cycling device to the pre-determined temperature associated with the thermal cycle will be greater than the amount of time to bring an individual vessel to the pre-determined temperature associated with the thermal cycle.

These shortcomings of batch processing can be addressed by a system and method that provide random access to each of the thermal cycles and that, moreover, provide individual temperature control over each vessel containing an aqueous solution.

U.S. Pat. No. 6,558,947 to Lund, et al. discloses a batch-type, thermal cycling device that enables one to control the temperature of each vessel well in the device independently of the temperature of adjacent vessel wells. This, however, only addresses half the problem because time is still spent filling up each of the 96 vessel wells before the thermal cycling device is batched.

Therefore, it would be desirable to provide a high-throughput system and testing method that provide random access to each of the thermal cycles and that provide individual temperature control over each vessel containing an aqueous solution.

SUMMARY OF THE INVENTION

A system and method for preparing a biological sample having an initial concentration of a nucleic acid (NA) for polymerase chain reaction (PCR) testing are disclosed. The system includes a nucleic acid isolation/purification apparatus and a PCR testing apparatus. The nucleic acid isolation/purification apparatus magnetically captures NA solids from the biological sample and then suspends the NA in elution buffer solution. The PCR testing apparatus subjects the eluted solution to multiple cycles of the denaturing, annealing, and elongating thermal cycles associated with PCR testing.

More specifically, the PCR testing apparatus includes a multi-vessel thermal cycler array that has a plurality of single-vessel thermal cyclers that are each individually-thermally controllable so that adjacent single-vessel thermal cyclers can be heated or cooled to different temperatures corresponding to the different thermal cycles of the respective PCR testing process.

BRIEF DESCRIPTION OF THE DRAWINGS

The invention will be better understood by reference to the following more detailed description and accompanying drawings where like reference numbers refer to like parts.

DETAILED DESCRIPTION OF THE INVENTION

The presently disclosed invention provides a random access system and a method using the system for isolating and purifying nucleic acid (NA) contained in a biological sample and for testing the biological sample, such as by polymerase chain reaction (PCR) testing. PCR testing is well-known to the art and will not be described in detail. Likewise, the "Boom patent" technique for isolating and purifying nucleic acid using magnetic particles referred to in this specification is the subject of U.S. Pat. No. 5,234,809 to Boom, et al., which is incorporated herein in its entirety by reference.

Figure 1:
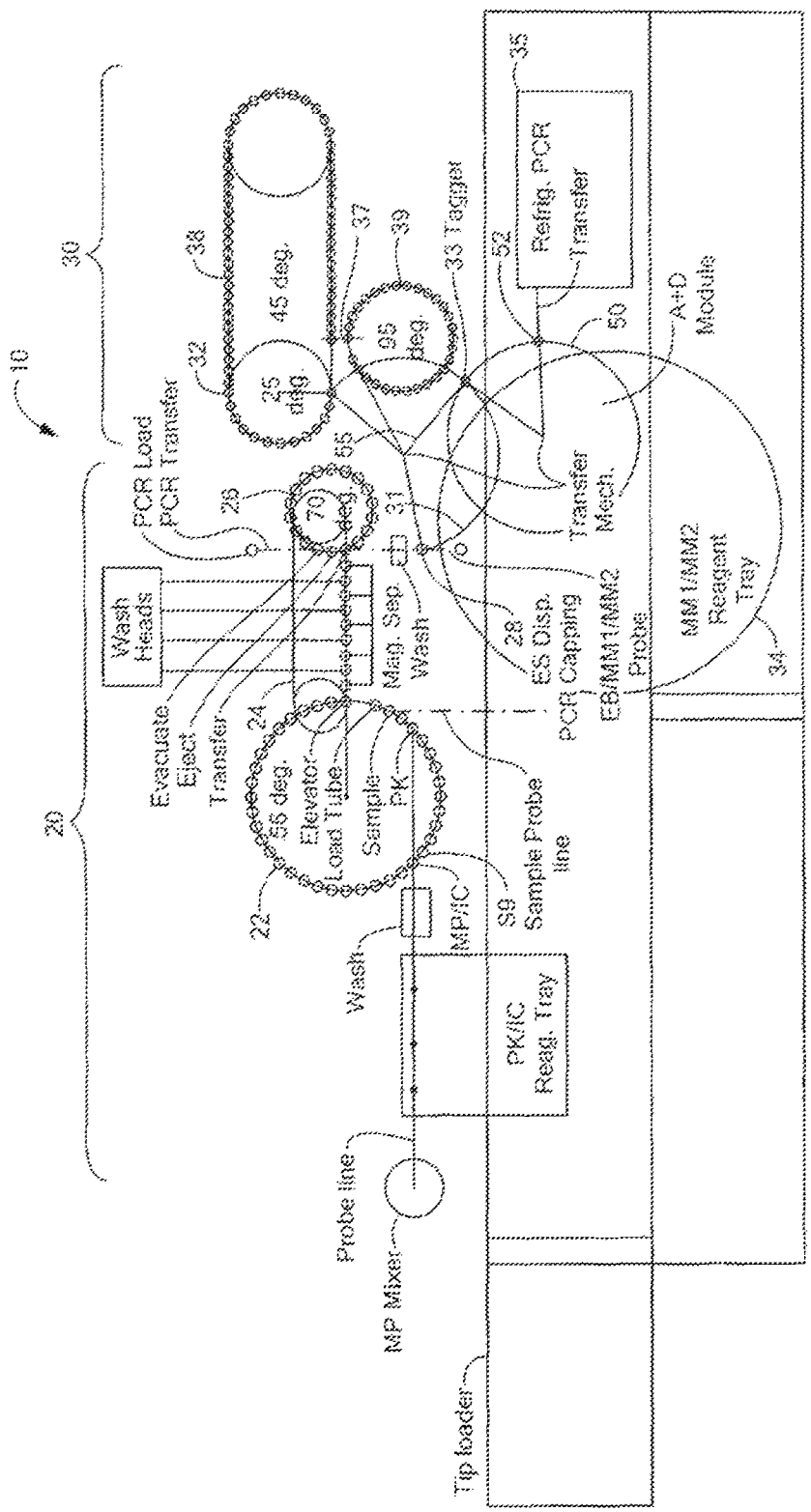
FIG. 1 shows a schematic of a random access system for PCR testing in accordance with the presently disclosed invention.
Figure 2:
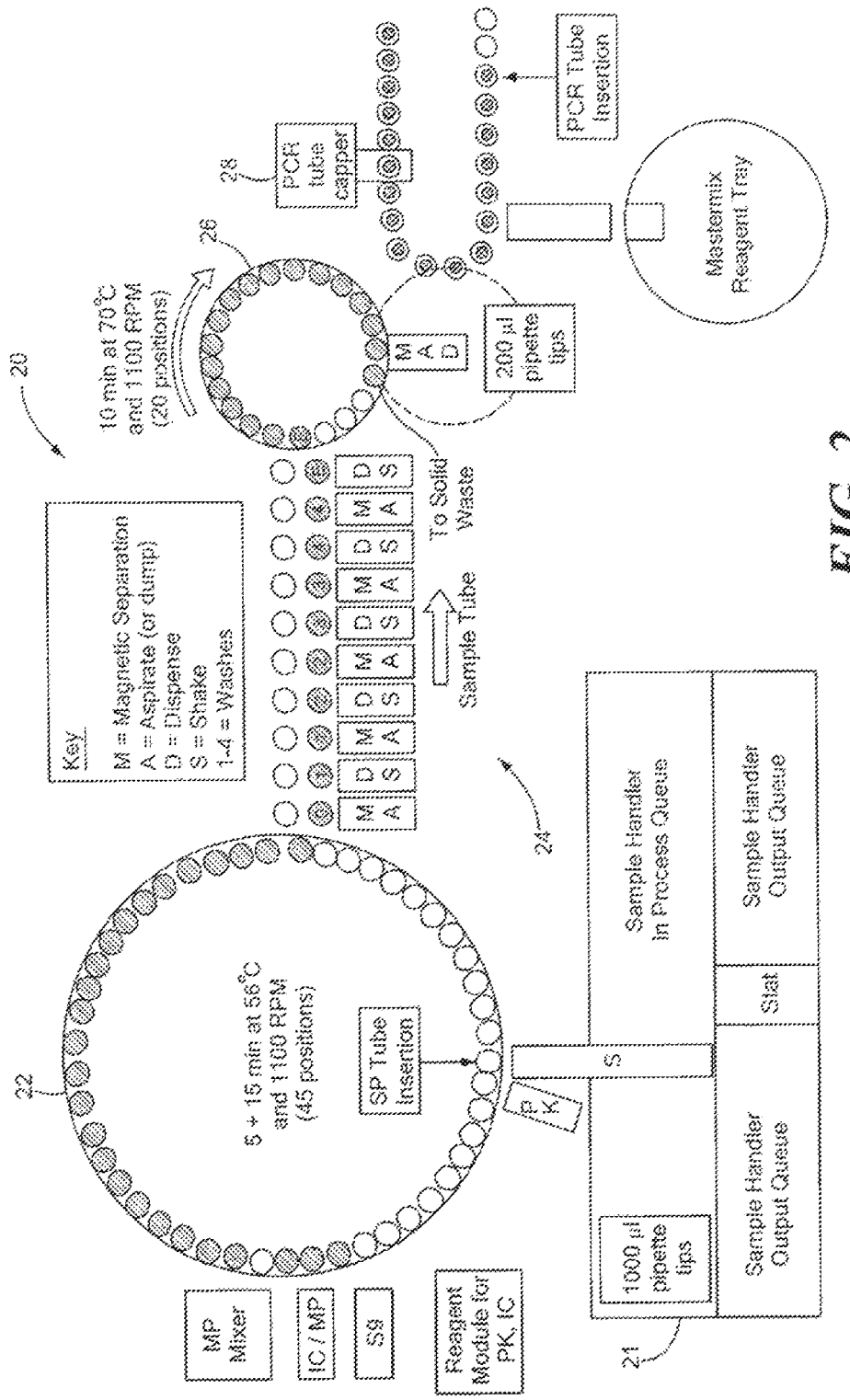
FIG. 2 shows the nucleic acid isolation/purification apparatus of the random access system for PCR testing in accordance with the presently disclosed invention.
Figure 3:
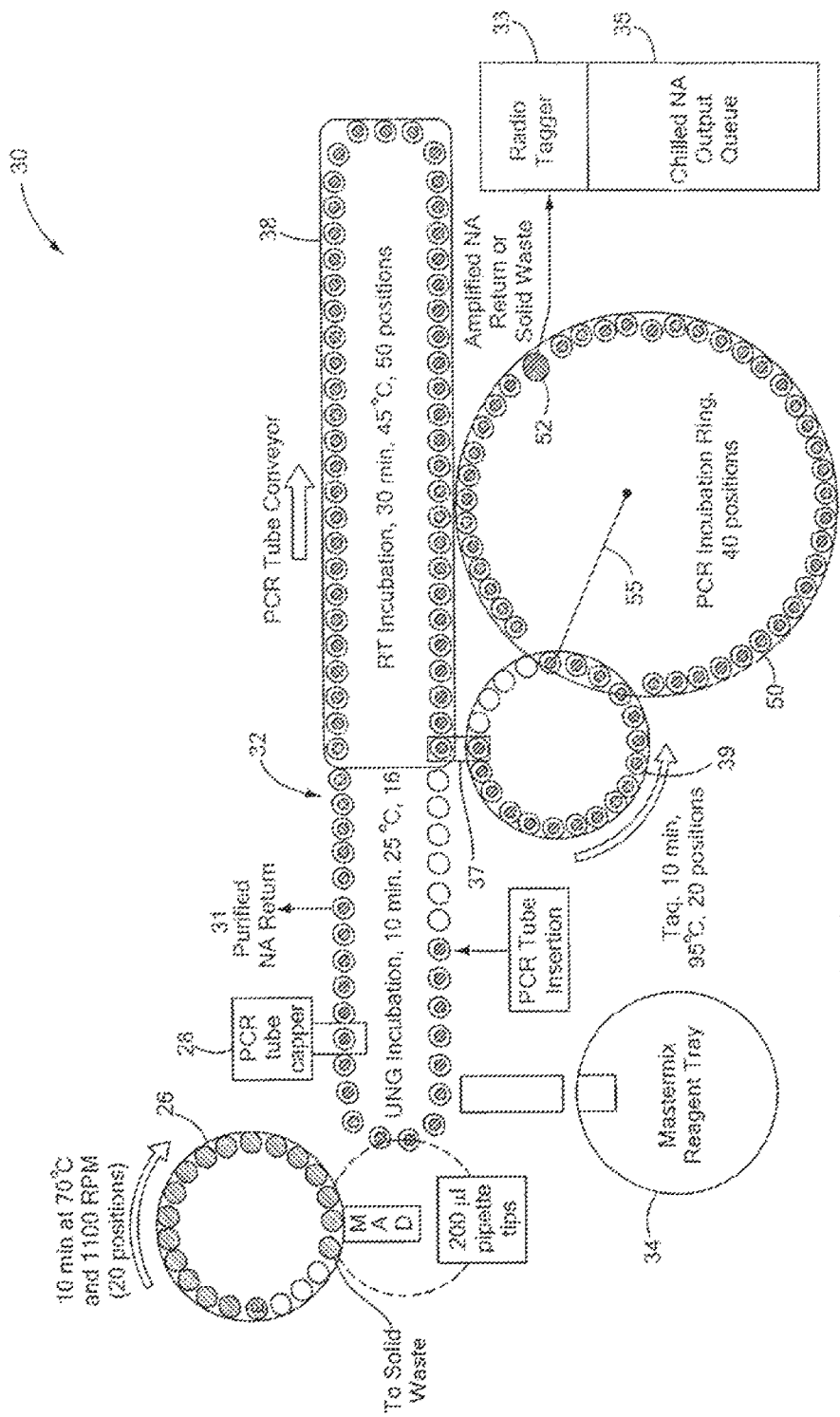
FIG. 3 shows the PCR testing apparatus of the random access system in accordance with the presently disclosed invention.

Referring to FIGS. 1-3, a random access system 10 for isolating and purifying NA contained in a biological sample and for testing the isolated and purified NA is shown. The system 10 provides high throughput and continuous testing of aqueous samples, i.e., "reaction liquids", containing some concentration of NA. NA is used herein to refer to single-stranded nucleic acid, i.e., RNA, and double-stranded nucleic acid, i.e., DNA.

The system 10 (FIG. 1) includes a nucleic acid (NA) isolation/purification apparatus 20 (FIG. 2) and a PCR testing apparatus 30 (FIG. 3), which are discussed separately below.

The Nucleic Acid Isolation/Purification Apparatus

The Boom patent discloses means for isolating and purifying NA in a biological material that initially contains some endogenous NA and/or some foreign NA. The Boom process is rapid, reproducible, and simple and the purified end product is undamaged and usable in other molecular biological reactions, such as PCR.

The Boom process begins by mixing the NA-carrying biological material, such as blood, serum, semen, urine, feces, saliva, tissue cultures, cell cultures, and so forth, with large amounts of a chaotropic substance in the presence of fine-grained silica particles. The chaotropic substance causes the biological material to lose all of its NA. The loosened NA is bound to the silica particles.

Chaotropic substances can include, without limitation, guanidine hydrochloride, guanidine (iso)thiocyanate, potassium iodide, sodium iodide, and the like. The NA-binding, solid-phase, silica particles can include glass powder, silicon oxide, silicon dioxide crystals, amorphous silicon oxide, and the like.

The solid, silica-NA complexes are than separated from, e.g., centrifically using a vortex, the aqueous solution. The aqueous solution is discarded. The solids are again washed with a chaotropic buffer and again subject to separation from the aqueous wash. This washing and separation process can be repeated multiple times.

The solid, silica-NA complexes are finally washed using a water-alcohol solution and acetone. The solution is dried to remove the acetone, leaving the solid, silica-NA complexes. The solid, silica-NA complexes are finally eluted with an aqueous elution buffer and the purified NA in solution, i.e., the "eluted solution", is recovered.

The NA isolation/purification apparatus 20 of the presently disclosed invention enables the practice of a method that generally follows the teachings of the Boom patent in isolating and purifying existing NA in a biological sample. Referring to FIGS. 1 and 2, samples containing a known or unknown concentration of NA are removed from a sample handler 21, such as used in the Advia Centaur® immunoassay system manufactured by the Siemens Medical Solutions Diagnostics of Tarrytown, N.Y., and dispensed in tubes in a vortex/incubation device 22. The circular vortex/incubation device 22 includes forty-five (45) positions to hold tubes and is capable of rotating at about 1100 revolutions per minute (RPM). NA samples are inserted and removed from the vortex/incubation device 22 on each cycle. Advantageously, unlike conventional batch processing, samples containing a different NA, such as HIV, HCV, HDB, and so forth, can be inserted randomly into the vortex/incubation device 22.

Those skilled in the art can appreciate that the number of positions in the circular vortex/incubation device 22 is a function of many things, including desired throughput and time. Therefore, use of a circular vortex/incubation device 22 having more or fewer positions than 45 is within the scope and spirit of this disclosure.

An enzyme for degrading the protein structure of the NA, such as proteinase K (PK), is added to the tube containing an NA sample and the mixture is incubated in the vortex/incubation device 22 at a temperature of about 56° C. for about five (5) minutes. A lysis buffer, such as S9, magnetic silica particles (MP), carrier RNA, and an Internal Control (IC) are then mixed in with the NA sample. Once the proteinase K enzyme degrades the protein structure of the NA sample, the lysis buffer releases the NA.

This mixture is then incubated and agitated in the vortex/incubation device 22 at about 56° C. for about fifteen (15) minutes. Incubation and agitation break down the NA-carrying sample, causing release of the NA from the sample. The released NA is then captured by the magnetic silica particles (MP). Alternative means of agitation can include, for example, ultrasound vibrations.

At the completion of each incubation and agitation cycle, the tubes carrying the NA sample are continuously and sequentially removed from the vortex/incubation device 22 and disposed on a sample tube conveyer 24, such as a conveyor belt having appropriately dimensioned receptacles. For example, tubes can be raised from the vortex/incubation device 22 to the tube conveyor 24 using a pneumatically-activated elevator (not shown).

While on the tube conveyor 24, the liquid lysis buffer, i.e., S9, and supernatant are separated, e.g., by aspiration, from the magnetic silica particles (MP) and the magnetic silica particles (MP) are washed. Each wash cycle includes dispensing an aqueous wash solution into the tube; agitating the tube to re-suspend the magnetic silica particles (MP); performing magnetic separation on the contents of the tube; and aspirating and discarding the aqueous solution. Four (4) washing cycles are an acceptable number; however, more or fewer washing cycles can be used, realizing that there may be greater NA isolation and purification from more washing cycles and less NA isolation and purification from fewer washing cycles.

Use of magnetic silica particles enables magnetic separation of the captured NA from the liquid lysis buffer and the supernatant. As previously mentioned, the solid, very fine-grained, magnetic silica particles capture the NA. After a washing solution is added to the tube, e.g., using a syringe pump, and the tube is agitated, re-suspending the NA-carrying, magnetic silica particles, a magnetic field is applied to the tube. In one embodiment, the magnetic field results from one or more magnets disposed adjacent select positions along the path of the tube conveyor 24. The magnetic field quickly attracts the NA-carrying, magnetic silica particles to one interior surface of the respective tube.

Tube agitation is accomplished on and by the conveyor belt 24. For example, a solenoid (not shown) can be mechanically-coupled to the conveyor belt's 24 drive pulley (not shown), such as a two-part, spring-loaded drive pulley. When the solenoid is activated, it causes the drive pulley and the conveyor belt 24 to vibrate. Alternatively, a drive motor (not shown) can be stepped back and forth at a pre-determined frequency, which will cause the conveyor belt 24 to shake.

After the final wash cycle, an elution buffer (E) is added to the NA-carrying, magnetic silica particles and the tube containing the eluted sample is transferred to another incubation/agitation ring 26, where the analyte-enriched NA is separated from the magnetic silica particles. The elution buffer (E) alters the pH of the magnetic silica particles in the eluted sample. In one embodiment, the tube containing the eluted sample is transferred to another incubation/agitation ring 26 by lowering the tube containing the eluted sample from the tube conveyor 24 to the incubation/agitation ring 26 using a pneumatically-activated elevator (not shown).

The incubation/agitation ring 26 shown in FIG. 2 includes twenty (20) positions to hold the tubes containing the eluted samples and is capable of rotation at a speed of about 1100 RPMs during incubation. Those skilled in the art can appreciate that the number of positions in the incubation/agitation ring 26 is a function of many things, including desired throughput and time. Therefore, use of a incubation/agitation ring 26 having more or fewer positions than twenty is within the scope and spirit of this disclosure.

The tubes containing the eluted samples are inserted and removed individually. Once all twenty positions of the incubation/agitation ring 26 have been filled with tubes, the tubes are incubated and agitated collectively as a group. Incubation and agitation occur for about ten (10) minutes at an incubation temperature of about 70° C. Once again, advantageously, unlike conventional batch processing, samples containing a different NA, such as HIV, HCV, HDB, and so forth, can be inserted randomly into the incubation/agitation ring 26.

The altered pH, incubation temperature, and agitation promote dissociation of the NA from the magnetic silica particles and re-suspension of the NA in the solution of the eluted sample. The eluted solution, which is an aqueous solution including the elution buffer and the NA-enriched sample in suspension, can then be separated from the solid, magnetic silica particles, e.g., by magnetic attraction and aspiration using a disposable pipette tip.

The eluted solution can be PCR tested immediately (as described below), or discrete tubes containing eluted solution can be capped and temporarily stored for testing at some later time as described below or discrete tubes containing eluted solution and a Mastermix reagent can be capped and temporarily stored for testing at some later time also as described below. The magnetic silica particles are disposed of.

In some applications, NA-purified, eluted samples may be desired for testing at a later time and/or place. For such instances, the system 10 includes a transfer point 31 after the wash cycle. More specifically, after washing and eluting, and separating the eluted solution from the magnetic silica particles, the tube containing the NA-purified, eluted solution can be transported to a capping device 28, where the tube containing the NA-purified, eluted samples is sealed or capped tightly. After capping, the eluted solution can be tagged, e.g., by radio frequency identification (RFID) using a radio "tagger" 33, and can then be stored in a refrigeration unit 35.

PCR Testing Apparatus

As provided in the description above, after separation of the magnetic silica particles from the eluted solution, the NA-purified, eluted solution is recovered from the tube, e.g., using a pipettor having a disposable tip. Referring to FIG. 3, the recovered eluted solution is dispensed into a removable, reaction vessel or cuvette 40 (hereinafter "cuvette") that is disposed temporarily on an incubation ring or conveyor belt 32. The cuvette 40 is structured and arranged to hold the reaction liquid (defined below) during at least one of capping and thermal cycling.

Preferably, the eluted solution is dispensed into a cuvette 40 that contains a Mastermix reagent, such as PCR Master-Mix reagent manufactured by Promega Corporation of Madison, Wis., (MM1 or MM2). Alternatively, the eluted solution can be added to the cuvette 40 first and the Mastermix reagent can be added afterwards. The aqueous solution comprising Mastermix reagents and the eluted solution is referred to as a "reaction liquid".

Mastermix reagents are well know to those skilled in the art and will not be described in greater detail. The composition of the Mastermix reagent, each of which is prepared in advance and stored in a reagent tray 34, differs depending on the NA being tested for, such as HIV, HCV, HDB, and so forth. Each Mastermix reagent includes the reagent uracil-DNA-gylcosylase (UNG). UNG is a reagent that is inactive at higher temperatures; but, at lower temperatures, such as ambient or room temperature, UNG destroys any NA copies that may still be mixed in with the reaction liquid. Thus, UNG is added to the reaction liquid to mitigate carryover contamination from the isolation/purification apparatus 20 into the PCR testing apparatus 30.

Once Mastermix reagent and the eluted solution have been added to a cuvette 40, a capping device 28 disposed along the incubation ring 32 seals or caps each cuvette 40 tightly. As mentioned previously, not all samples or, in this case, reaction liquids are prepared for immediate PCR testing. In some instances, it may be desirable to test discrete reaction liquids at a later time or place. In such instances, discrete, capped, cuvettes 40 containing reaction liquids that have been UNG-incubated, can be removed from the incubation ring 32 at a transfer point 31 whence they can be transferred to a tagging device 33, such as an RFID radio "tagger". The capped, cuvettes 40 so removed can be tagged and then stored in a refrigeration unit 35.

As shown in FIG. 3, in an illustrative embodiment, the incubation ring 32 includes sixteen (16) positions to hold cuvettes 40 and the conveying belt is capable of advancing continuously at a rate so that each cuvette 40 spends approximately ten (10) minutes processing along the incubation ring 32. The temperature of the incubation ring 32 is maintained at about 25° C.

Those skilled in the art can appreciate that the number of positions in the incubation ring 32 is a function of many things, including desired throughput and time. Therefore, use of an incubation ring 32 having more or fewer positions than sixteen is within the scope and spirit of this disclosure.

As the conveying belt of the incubation ring 32 continues to advance, capped, UNG-incubated cuvettes 40 containing reaction liquid are further incubated in an RT incubation portion 38, e.g., an oven, at a temperature of about 45° C. The purpose of incubating the cuvettes 40 at a temperature of about 45° C. is for converting any single-stranded RNA samples into double-stranded DNA prior to PCR testing. More particularly, the Mastermix reagent added to cuvettes 40 that contain RNA samples instead of DNA samples will include reverse transcriptase (RT), a DNA polymerase enzyme that transcribes single-stranded RNA into double-stranded DNA.

As shown in FIG. 3, the RT incubation portion 38 includes fifty (50) positions to hold cuvettes 40 and the incubation ring 32 is capable of advancing incrementally or continuously at a rate so that each cuvette 40 spends approximately thirty (30) minutes undergoing RT incubation. Those skilled in the art can appreciate that the number of positions in the RT incubation portion 38 of the incubation ring 32 is a function of many things, including desired throughput and time. Therefore, use of an RT incubation portion 38 having more or fewer positions than 50 is within the scope and spirit of this disclosure.

The PCR testing apparatus 30 is further structured and arranged so that the point of termination of the RT incubation portion 38 is proximate to a PCR transfer point 37. As a result, at the completion of RT incubation, each capped, RT-incubated cuvette 40 is transferred from the incubation ring 32 to a denaturing heating station ring 39.

As shown in FIG. 3, the denaturing heating station ring 39 includes sixteen (16) positions to hold cuvettes 40. The ring 39 is capable of advancing incrementally or continuously at a rate so that each cuvette 40 spends approximately ten (10) minutes undergoing the denaturing thermal cycle. Those skilled in the art can appreciate that the number of positions in the denaturing heating station ring 39 is a function of many things, including desired throughput and time. Therefore, use of a denaturing heating station ring 39 having more or fewer positions than sixteen is within the scope and spirit of this disclosure.

During the denaturing thermal cycle, each capped cuvette 40 is heated to a temperature between approximately 90 and 95° C., e.g., using an oven, to activate the polymerase enzyme (typically Taq) in the reaction liquid. As mentioned above, at approximately 90 and 95° C., the DNA double helix is melted so that each strand of the double helix is separated from the other.

The capped cuvette 40 containing denatured NA is then transferred to any vacant cuvette well 52 in an amplification and detection (A+D) module 50. Preferably, the cuvettes 40 are transferred using a radial arm 55 that is structured and arranged to pick-up the capped cuvette 40 from the denaturing heating station ring 39 and depositing it in a vacant cuvette well 52.

The A+D module 50 is a thermal cycler array having forty (40) individually-controllable, single-vessel thermal cyclers that are structured and arranged to hold cuvettes 40 during the initial annealing and initial elongation thermal cycles and during all subsequent thermal cycles of the PCR process. Those skilled in the art can appreciate that the number of individually-controllable, single-vessel thermal cyclers in the A+D module 50 is a function of many things, including desired throughput and time. Therefore, use of an A+D module 50 having more or fewer individually-controllable, single-vessel thermal cyclers than forty is within the scope and spirit of this disclosure.

While each capped cuvette 40 is disposed in a respective cuvette well 52, the initial annealing and initial elongation thermal cycles of the PCR process are conducted at appropriate, pre-determined temperatures ranging between approximately 50 and 65° C. (for annealing) and between approximately 70 and 72° C. (for elongation), respectively. After each complete PCR cycle, the light intensity of each reaction liquid is detected and measured. Once the light intensity reaches or exceeds a pre-determined threshold intensity, $I_{TH}$, the initial DNA concentration of the NA sample can be estimated, for example using look-up tables.

Figure 5:
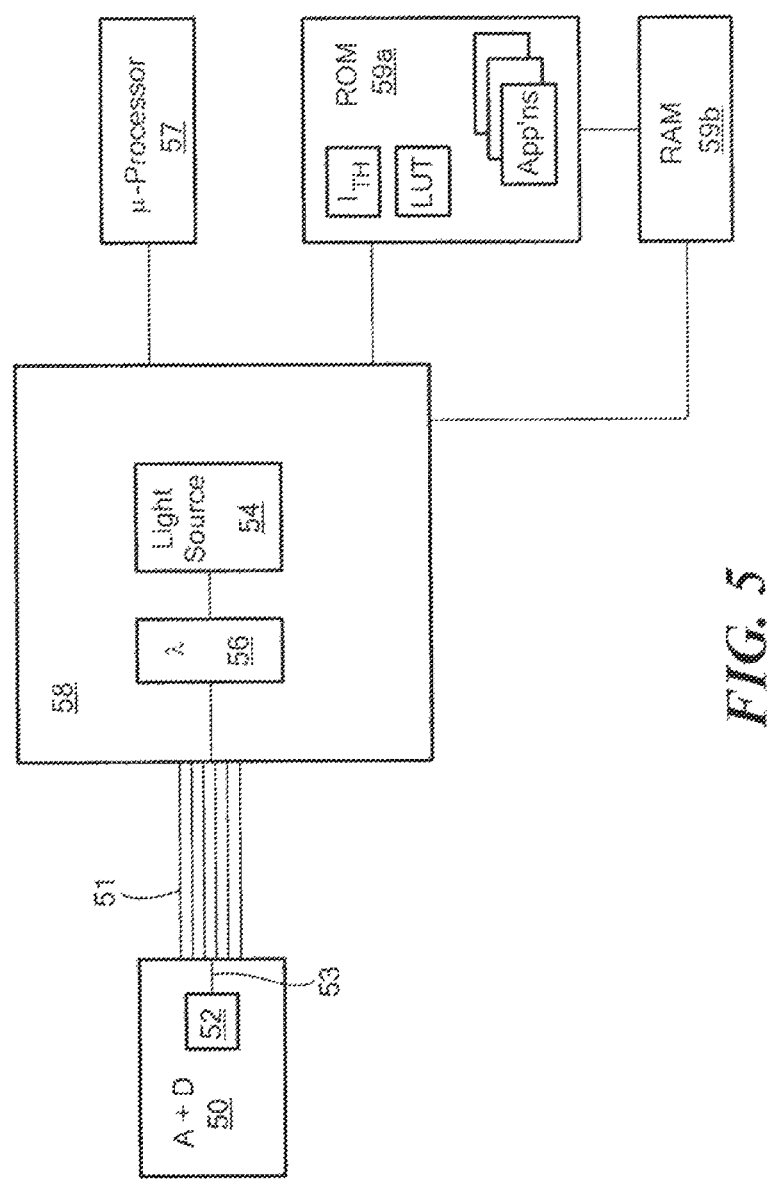
FIG. 5 shows a block diagram of a fluorimeter and the amplification and detection device in accordance with the presently disclosed invention.

Referring to FIG. 5, the A+D module 50 is in operational association with a fluorimeter 58 via a fiber-optic bundle 51. More specifically, at least one optical fiber 53 of the fiber-optic bundle 51 is structured and arranged to be optically-coupled to each cuvette well 52 and, more particularly, each cuvette 40 is optically-transmissive at required wavelengths. Each optical fiber 53 is optically-coupled to the fluorimeter 58 so that the intensity of light of reaction liquid can be measured at a plurality of wavelengths, such as four (4), following each complete PCR cycle.

The fluorimeter 58 includes multiple, such as four (4), light sources (not shown) having different wavelengths or a single light source 54 having a narrowband wavelength in combination with a filter wheel 56 that can produce different wavelengths. When a single light 54 source is used, light from the fluorimeter 58 at a first wavelength illuminates the reaction liquid disposed in each cuvette well 52 via at least one associated optical fiber 53. The fluorescence signal from the reaction liquid is transmitted back to the fluorimeter 58 via at least one associated optical fiber 53. The fluorimeter 58 detects or measures the intensity level of the fluorescence signal. This process is repeated for at least three different wavelengths for each cuvette well 40 containing a reaction liquid.

The fluorimeter 58 also includes or is in operational association with a processing unit 57 and memory components 59a and 59b. Non-volatile memory 59a can store applications or driver programs for operation of the fluorimeter 58, threshold intensity data, $I_{TH}$, and/or look-up tables, LUT, correlating measured intensity level and number of PCR amplification cycles to estimate initial DNA concentration levels, and so forth. Memory component 59b can include volatile, random access memory (RAM) for running one or more of the applications or driver programs.

During operation of the system 10 and the PCR testing apparatus 30, the intensity of a detected fluorescence signal at a particular wavelength, $I_m$, can be compared with a common, pre-determined threshold intensity, $I_{TH}$, applicable to all reaction liquids or with a pre-determined threshold intensity, $I_{TH}$, applicable to a specific reaction liquid. When the detected intensity level of the fluorescence signal exceeds the threshold intensity ($I_m > I_{TH}$), look-up tables (LUT) can be used to correlate the initial NA concentration with the measured intensity level, $I_m$, wavelength, and number of amplification cycles, n. The initial concentration for each reaction liquid (corresponding to an NA sample) can be recorded and saved in volatile or non-volatile memory 59b or 59a.

Once initial concentration data for reaction liquid have been recorded, the cuvette 40 containing the reaction liquid can be removed from the A+D module 50 to await final disposition. Optionally, the cuvettes 40 can be tagged by the RFID radio tagger 33 and stored in the refrigeration unit 35.

Single-Vessel Thermal Cycler

As provided above, the A+D module 50 is a circular, thermal cycler array having a plurality, e.g., forty (40), individually-controllable, single-vessel thermal cyclers. The single-vessel thermal cyclers are structured and arranged to hold each cuvette 40 in a seat. Moreover, while each cuvette 40 is disposed in a seat in the A+D module 50, the temperature of the cuvette 40 during the initial annealing and initial elongation thermal cycles and during all subsequent thermal cycles of the PCR process can be controlled individually. Individual thermal control and the capability to continuously insert cuvettes 40 into and/or extract cuvettes 40 from the A+D module 50 makes random access testing possible and practical.

Figure 4:
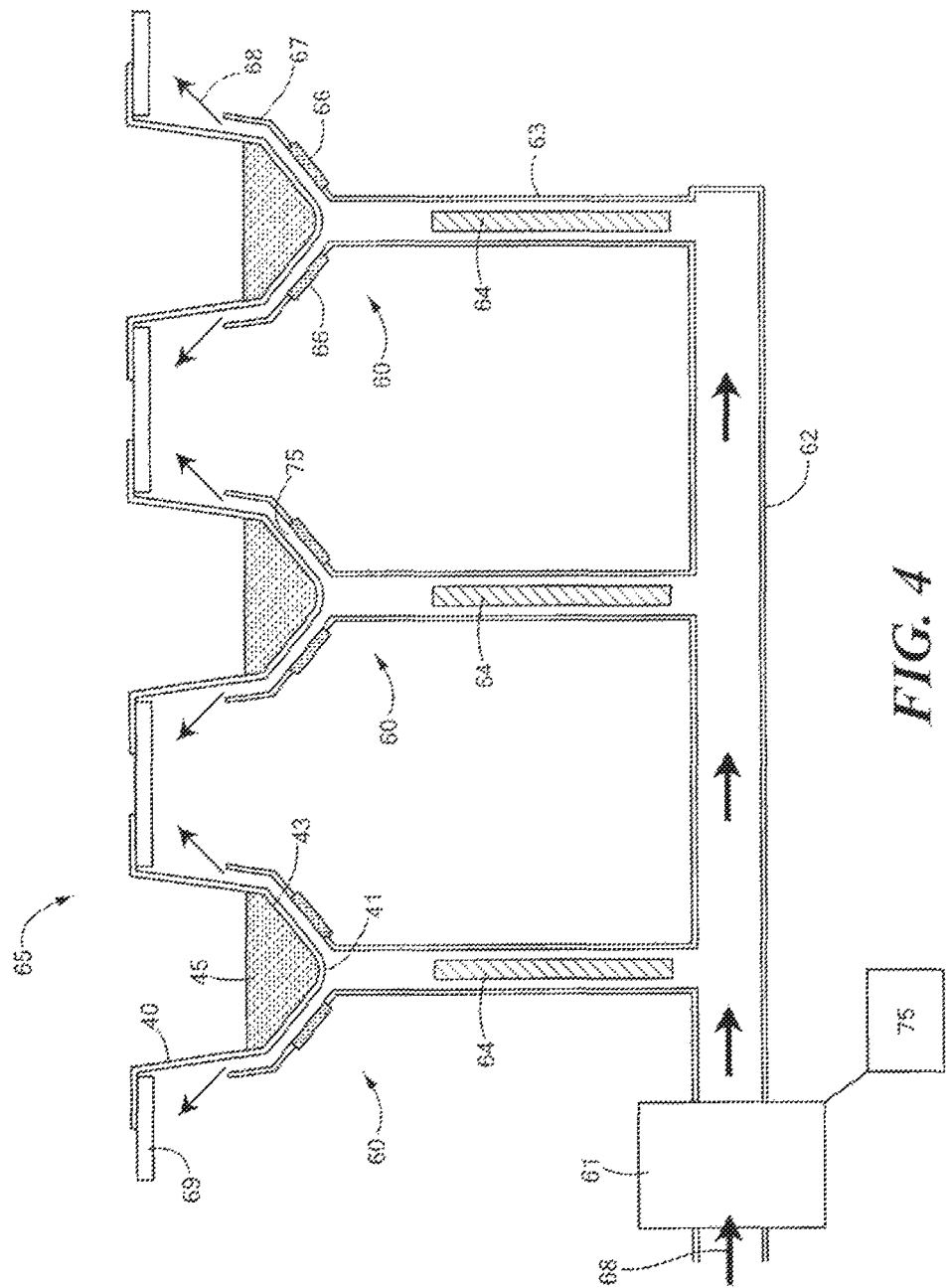
FIG. 4 shows a single-vessel thermal cycler for individually heating cuvettes containing reaction liquid disposed in an amplification and detection device in accordance with the presently disclosed invention.

Referring to FIG. 4, a valve-less, multi-vessel thermal cycler array 65 having a plurality of single-vessel thermal cyclers 60 is shown. Although the invention is described using a valve-less approach, valve-based approaches for thermally-controlling the cuvettes 40 can also be used without violating the scope and spirit of this disclosure. Advantageously, valve-based control systems may be quicker and may offer more precise temperature control. Disadvantageously, valve-based control systems are more expensive, more complex, and less reliable.

The multi-vessel thermal cycler array 65 includes a plurality of seats 69 for accommodating or mounting radially-symmetrical cuvettes 40 containing reaction liquid. The seats 69 are structured and arranged to provide precise positioning of the cuvettes 40 with respect to the respective heating assembly (described below). Preferably, the seats 69 are coaxial with a gas-to-vessel flow guide 67 (described below). More preferably, the seats 69 do not physically contact the gas-to-vessel flow guide 67 so as to provide an air gap 75 between the bottom portion of the cuvette 40 and the gas-to-vessel flow guide 67.

The seats 69 also may include a slight tilt in combination with a V-notch (not shown) or some other element or aspect as a centering feature. Optionally, the seats 69 can be structured and arranged to vibrate the reaction liquid 45 in the cuvette 40, for example, to reduce temperature gradients in the reaction liquid 45 and/or to out-gas bubbles that may obstruct optical viewing. For example, each vessel seat 69 can be an electrically-actuated, AC-driven, piezoelectric disk having a center hole region in which the cuvette 40 can sit.

To provide independent thermal control, each single-vessel thermal cycler 60 includes a heating assembly and a gas-to-vessel flow guide 67. The heating assembly includes a heating element 64, such as an electrically-resistive heating element, which is disposed inside a tubular, gas-to-heater flow guide 63. The gas-to-heater flow guide 63 confines and distributes gas flow 68 relative to the heating element 64 to achieve the proper heat transfer between the heating element 64 and the gas 68.

The gas-to-vessel flow guide 67 acts as an outer shell of the "heat exchanger". More specifically, the gas-to-vessel flow guide 67 is a shroud-like device that is structured and arranged to promote gas-to-vessel heat exchange by distributing the flow of gas 68 across a region including the cuvette's 40 outer surface area 41 that corresponds to the reaction liquid-wetted, inner surface area 43. The gas-to-vessel flow guide 67 also includes an optically-transmissive region(s) 66 that, preferably, is/are in operational association with the optical-fiber(s) 53 of the fiber-optics bundle 51 described above.

Gas 68, which can be a single gas or a mixture of gases, is the working fluid for heat exchange with the cuvette 40. A gas flow driver 61, such as an air compressor or diaphragm-type air pump, can be used to deliver gas 68 through a main conduit 62 to each of the gas-to-vessel flow guides 67.

A controller 75 having a processing unit and volatile and non-volatile memories is electrically-coupled to the gas flow driver 61 as well as to each of the heating elements 64. The controller 75 controls the rate of gas 68 flow to the gas-to-vessel flow guides 67. The controller also controls the timing and amount of current to each heating element 64 for the purpose of controlling the heat exchange between the resistive heating elements 64 and the gas 68 for each gas-to-vessel flow guide 67, independent of any other gas-to-vessel flow guide 67. Thus, at any point in time, the temperature on any cuvette 40 is vessel specific and independently variable.

Attainable air temperature change characteristics using, for example, 5.4 liter/minute air flow and electrical heating of a coil of NiCr wire include a heating change rate of about 3.7° C./second from 60° C. to 90° C. and a cooling rate of about 2.5° C./second from 90° C. to 60° C.

The invention has been described in detail including the preferred embodiments thereof. However, those skilled in the art, upon considering the present disclosure, may make modifications and improvements within the spirit and scope of the invention.

What we claim is:

1. A system comprising:
   a thermal cycler array having
      a plurality of wells arranged in a circular array, each well arranged to accommodate a single reaction vessel containing a reaction liquid,
      a plurality of resistive heating elements, each proximately located to a different one of the wells, and
      a plurality of flow guides, each arranged to direct heat generated by one of the resistive heating elements to only one of the wells; and
   a controller configured to independently control the amount of current delivered to each resistive heating element.

2. The system of claim 1, further comprising:
   an arm arranged to deliver a reaction vessel to one of the plurality of wells.

3. The system of claim 2, further comprising:
   a denaturing heating station, from which the arm delivers the reaction vessel to one of the plurality of wells.

4. The system of claim 3, wherein the denaturing heating station is arranged as a rotatable ring.

5. The system of claim 1, further comprising a fluorimeter in operational association with the plurality of wells via a plurality of optical fibers.

6. The system of claim 5, wherein each flow guide includes an optically-transmissive region in operational association with at least one of the plurality of optical fibers.

7. The system of claim 1, further comprising:
   a gas source; and
   a gas flow driver for providing pressurized gas from the gas source to each of the plurality of flow guides, wherein each of the resistive heating elements is arranged to variably heat the pressurized gas before the pressurized gas reaches each respective flow guide.

8. The system of claim 1, wherein each of the plurality of wells is structured and arranged to include at least one of a slight tilt, a V-notch, and a reaction vessel centering feature.

* * * * *